(12) United States Patent
Derendorf et al.

(10) Patent No.: US 6,904,309 B2
(45) Date of Patent: Jun. 7, 2005

(54) MICRODIALYSIS PROBES AND METHODS OF USE

(75) Inventors: Hartmut Derendorf, Gainesville, FL (US); Markus Mueller, Vienna (AT)

(73) Assignee: University of Florida, Gainesville, FL (US)

(*) Notice: Subject to any disclaimer, the term of this patent is extended or adjusted under 35 U.S.C. 154(b) by 243 days.

(21) Appl. No.: 10/177,011

(22) Filed: Jun. 21, 2002

(65) Prior Publication Data

US 2003/0009100 A1 Jan. 9, 2003

Related U.S. Application Data

(60) Provisional application No. 60/300,398, filed on Jun. 22, 2001.

(51) Int. Cl.[7] .................................................. A61B 5/05
(52) U.S. Cl. ...................................... 600/427; 600/420
(58) Field of Search ................................ 600/427, 425, 600/429, 431, 410, 411, 407, 420; 250/302, 303; 424/9.3, 9.1

(56) References Cited

U.S. PATENT DOCUMENTS

| | | | |
|---|---|---|---|
| 4,694,832 A | | 9/1987 | Ungerstedt |
| 5,106,365 A | | 4/1992 | Hernandez |
| 5,191,900 A | | 3/1993 | Mishra |
| 5,201,314 A | | 4/1993 | Bosley et al. |
| 5,607,390 A | | 3/1997 | Patsalos et al. |
| 5,706,806 A | | 1/1998 | Kissinger |
| 5,741,284 A | * | 4/1998 | Karlsson ............ 604/160 |
| 5,919,135 A | * | 7/1999 | Lemelson ............ 600/407 |
| 6,106,473 A | | 8/2000 | Violante et al. |
| 6,487,438 B1 | * | 11/2002 | Widmark et al. ...... 600/431 |
| 6,493,570 B1 | * | 12/2002 | Dees et al. .......... 600/411 |
| 6,658,279 B2 | * | 12/2003 | Swanson et al. ...... 600/407 |
| 6,675,037 B1 | * | 1/2004 | Tsekos ............. 600/417 |
| 6,723,084 B1 | * | 4/2004 | Maginot et al. ....... 604/535 |

FOREIGN PATENT DOCUMENTS

| | | |
|---|---|---|
| DE | 90 02 100 | 7/1990 |
| WO | WO 01/03752 A1 | 1/2001 |
| WO | WO 01/03763 A1 | 1/2001 |

OTHER PUBLICATIONS

Muller, M. et al. "In vivo characterization of transdermal drug transport by microdialysis" *J. Controlled Release*, 1995, 37:49–57.

Muller, M. "Microdialysis in clinical drug delivery studies" *Adv. Drug Deliv. Reviews*, 2000, 45:255–269.

Muller, M. et al. "*In vivo* drug–response measurements in target tissues by microdialysis" *Clin. Pharmacol. Ther.*, Aug. 1997, 62:165–170.

Ronquist, G. et al. "Treatment of Malignant Glioma by a New Therapeutic Principle" *Acta Neurochir* (*Wien*), 1992, 114:8–11.

* cited by examiner

*Primary Examiner*—Daniel Robinson
(74) *Attorney, Agent, or Firm*—Saliwanchik, Lloyd & Saliwanchik

(57) ABSTRACT

The subject invention pertains to novel microdialysis probes having highly advantageous structural features, particularly for clinical applications. A microdialysis probe of the subject invention can be introduced into a biological tissue using insertion means such that the insertion means can the be completely dissociated from the biological tissue and the microdialysis probe. The microdialysis probes of the subject invention can further include guiding means composed of imageable material that may be used to guide the microdialysis probes to a target tissue using the appropriate sensing equipment. A further aspect of the subject invention relates to methods of using novel microdialysis probes to assess the presence or absence of a substance within biological tissue. The subject invention further relates to methods of using novel microdialysis probes to deliver a substance within biological tissue.

81 Claims, 6 Drawing Sheets

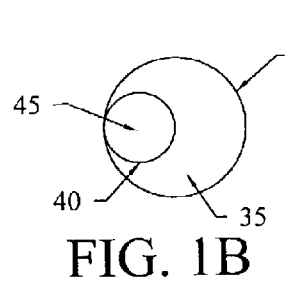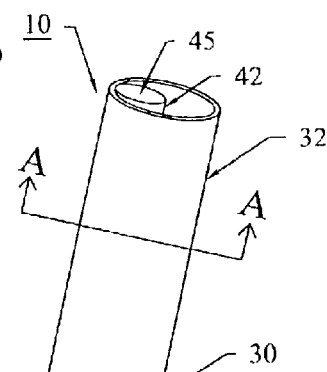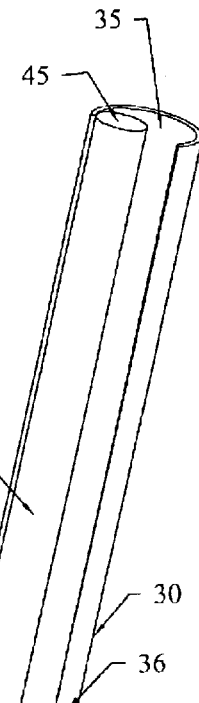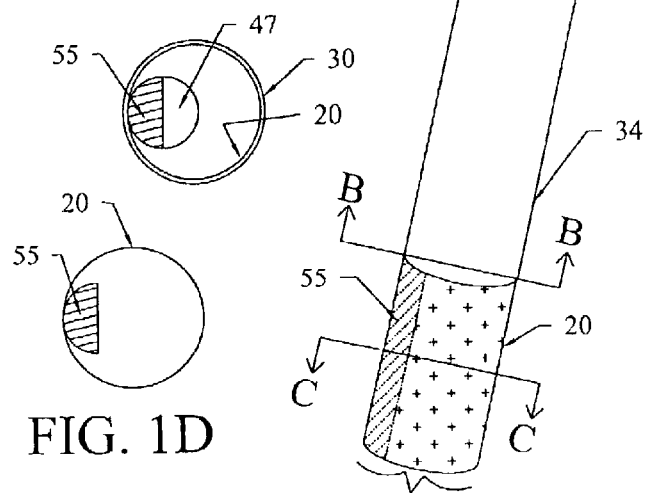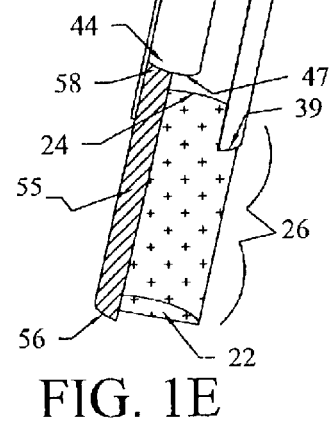
FIG. 1B
FIG. 1C
FIG. 1D
FIG. 1A
FIG. 1E

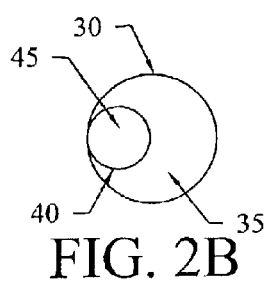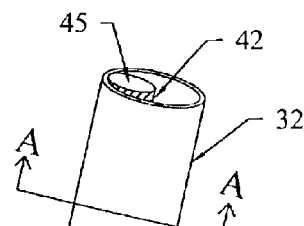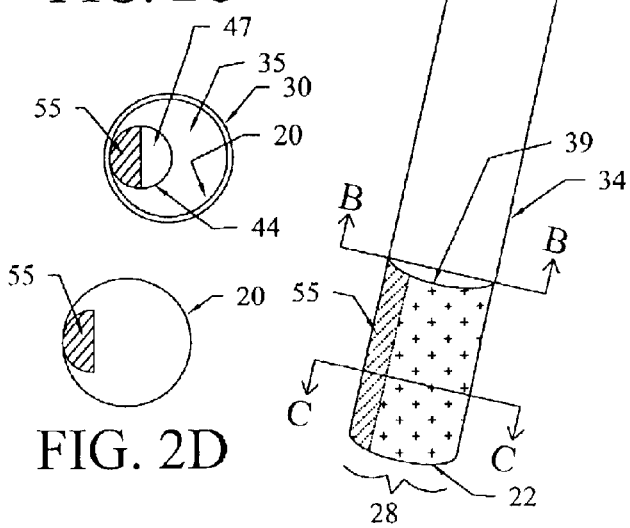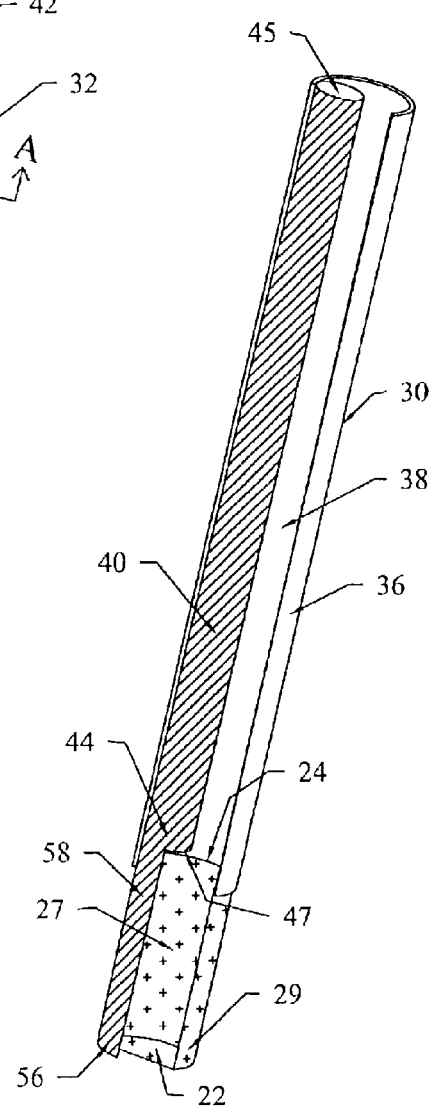

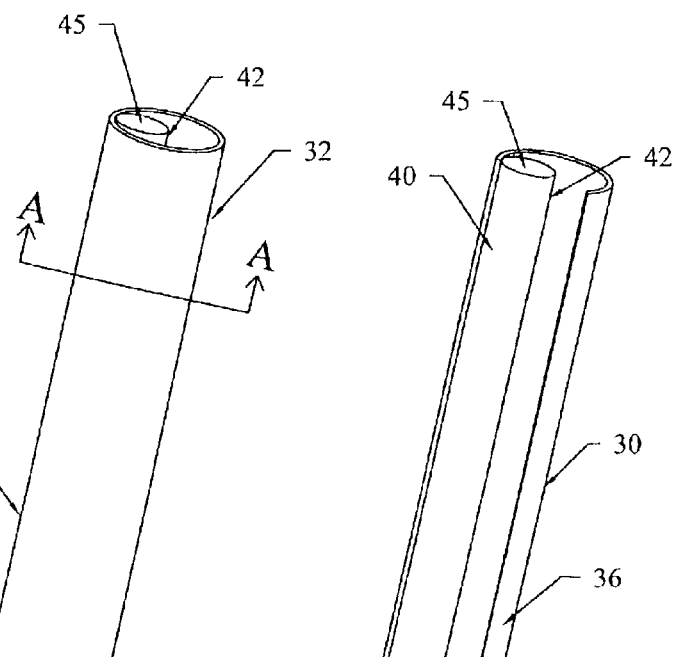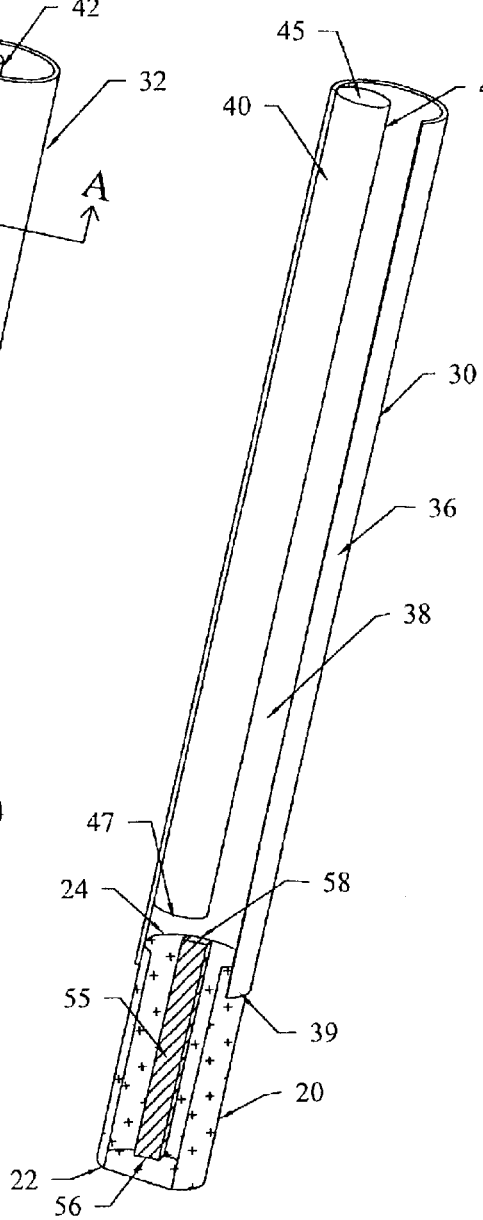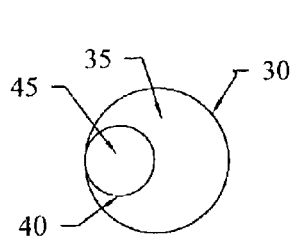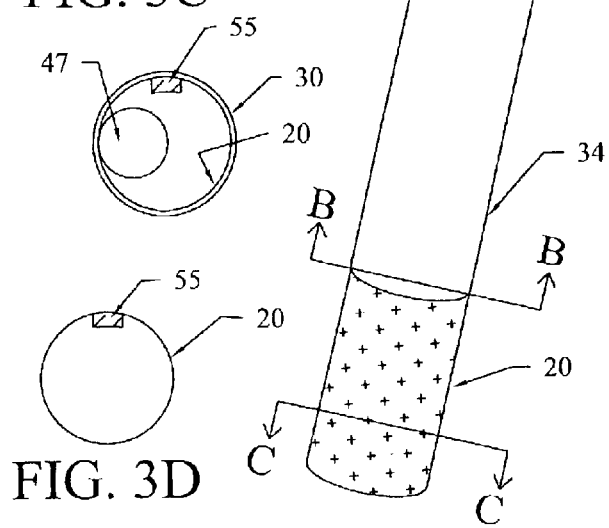
FIG. 3B
FIG. 3C
FIG. 3D
FIG. 3A
FIG. 3E

MICRODIALYSIS PROBES AND METHODS OF USE

CROSS-REFERENCE TO RELATED APPLICATION(S)

This application claims the benefit of provisional patent application Ser. No. 60/300,398, filed Jun. 22, 2001, which is hereby incorporated by reference in its entirety, including all figures, tables, and drawings.

BACKGROUND OF THE INVENTION

Microdialysis is a technique used to monitor the chemistry of the extracellular or interstitial space in biological tissue. For many years, the use of microdialysis sampling in research and therapeutics has proven to have many advantages, such as clean samples, more frequent samples, and conservation of body fluid. In addition, microdialysis provides a direct profile of substances within tissues of interest, whereas many conventional methods depend upon calculating the tissue concentration indirectly from serial blood samples. Therefore, microdialysis provides a preview of chemical changes in the tissue before those events are reflected as chemical changes in the blood.

A microdialysis probe is a device that is introduced into tissue and is designed to mimic a blood capillary in function. When a physiological salt solution, called the perfusion fluid or dialysis medium (e.g., Ringer solution), is slowly perfused through the microdialysis probe, it draws chemical substances from the extracellular space into the probe as it equilibrates with the extracellular fluid such that the probe will eventually contain a representative proportion of molecules found in the extracellular space. Therefore, the microdialysis technique allows the investigation of discrete local tissue function directly at the cellular level and is well suited for diagnostic applications involving metabolism, endocrinology, toxicology, pharmacokinetics, neurotransmission, and other studies.

Various designs of microdialysis probes have been developed for particular sites or types of tissues. For example, microdialysis probes can be flexible or rigid, and the in and out flow paths can be looped, side-by-side, or concentric, as described in U.S. Pat. No. 5,191,900. In a concentric probe design, the perfusion medium typically enters the probe through an inner tube and is pumped slowly to the distal end of the inner tube where it flows into the tip of the probe, which is surrounded by the dialysis membrane. This is the site of dialysis, i.e., diffusion of substances across and back from the extracellular fluid. The resulting dialysate exits the probe by flowing through a larger outer tube, where it is collected for analysis.

Dialysis is bi-directional in that there is exchange of molecules in both directions across the membrane. The difference in the concentration of a specific molecule across the dialysis membrane will determine the direction of the diffusion gradient. As a result of this property, the microdialysis technique not only allows measurement and quantification of endogenous molecules, the technique can also be used for site-specific drug delivery to the extracellular space (Rongquist, G. et al. [1992] Treatment of Malignant Glioma by a New Therapeutic Principle" *Acta Neurochir* 114:8–11; Muller, M. et al. [1997] In vivo Drug Response Measurements in Target Tissues by Microdialysis" *Clin Pharmacol Ther* 62:165–170). For example, one can collect an endogenous substance, such as neurotransmitter, and at the same time introduce an exogenous substance, such as a receptor agonist or antagonist, into the extracellular space.

The microdialysis technique has become more popular in recent years and a number of significant advances have been made. The use in clinical and research applications on humans has been slow, however, primarily because microdialysis probes are naturally fragile, which makes them difficult to insert. At least one part of the probe must have a surface that is composed of the thin, semi-permeable dialysis membrane, which is easily broken.

Many microdialysis probes are introduced into tissue by first inserting a metal needle into the lumen of a plastic insertion cannula (also referred to as a guide cannula), such that the pointed tip of the needle extends beyond the distal end of the insertion cannula. The needle and cannula are then inserted into the tissue, with the needle tip piercing the tissue. The needle is then slid from the lumen of the insertion cannula, leaving only the insertion cannula in the tissue. A microdialysis probe is then inserted into the lumen of the insertion cannula so that the membrane at the distal end of the probe extends just beyond the distal end of the insertion cannula, into the tissue, where the needle tip had previously extended. Therefore, the insertion cannula permits insertion of the probe with minimal damage to the tissue beyond that caused by the needle.

Alternatively, the insertion cannula can itself define a pointed cutting edge at its distal end, eliminating the necessity of inserting a needle through the cannula and into the tissue. The microdialysis probe is then inserted into the lumen of the pointed insertion cannula. However, this arrangement is more traumatic and the lumen of the insertion cannula can become fouled with tissue upon insertion.

A conventional microdialysis probe usually includes at its proximal end a connecting part for connection to an ingoing and an outgoing hose or tubing. Because this connecting part typically has a larger outer diameter than the inner diameter of the insertion cannula, the insertion cannula cannot simply be slid over the connecting part. Some connecting parts also have one or more hoses that extend perpendicularly to the longitudinal axis of the probe, which also prevents easy removal of the insertion cannula. Therefore, the insertion cannula must remain in the tissue at the insertion site and cannot be removed until the probe is removed. Microdialysis probes of this type are described in U.S. Pat. Nos. 4,694,832 and 5,106,365. In some microdialysis probes with which the insertion cannula is left in situ, the probes further include an anchoring member at their distal end, which engages (e.g., screws into) the end of the insertion cannula, indirectly attaching the probe to the outside of the subject's body. Examples of such probes are described in U.S. Pat. No. 5,607,390.

These conventional probes have inherent problems when inserted into deeper tissues, such as organs. For example, when inserting a microdialysis probe into a lung, it is first necessary to make a surgical incision in the skin and the underlying chest wall. Due to the presence of the insertion cannula and any laterally projecting parts (e.g., connecting parts, anchoring member), the incision must be left open during sampling and/or drug delivery. This situation increases expense, as well as the risk of surgical complications, such as infection. In addition, because the insertion cannula and connecting part are often rigid, their presence can cause trauma to moving tissues (e.g., lung, muscle) that come in contact with these devices.

In an alternative design, the probe is inserted through a cannula tube (i.e., insertion cannula) and the cannula tube has a longitudinal slot, as described in U.S. Pat. No. 5,741,284. After the cannula tube is inserted into the tissue and the probe is inserted into the cannula tube, the cannula tube can be withdrawn because the probe can pass through the longitudinal slot of the cannula tube. The microdialysis probe also has a laterally extending wing mounted on its proximal end. The wing is held firmly during removal of the cannula tube so that the probe is not withdrawn from the tissue along with the cannula tube. After the cannula tube has been withdrawn and discarded, the wing is folded down against the skin and secured thereto with adhesive tape. While this arrangement may be used for insertion of the probe through the skin and soft underlying tissues, it would be less practical to insert this probe into deeper tissues, such as organs, which may necessitate a surgical incision through the chest wall. Due to the presence of the wing, the incision would have to be left open during sampling and/or drug delivery.

Alternatively, the insertion cannula can be designed to be "rupturable". Such cannulas are also described in U.S. Pat. No. 5,607,390. A rupturable insertion cannula is typically constructed with longitudinal weakenings (e.g., perforations) such that the cannula can be pulled apart into two or more pieces and eliminated, leaving only the microdialysis probe positioned within the tissue. Hence, the rupturable insertion cannula is sometimes referred to as "split plastic tubing" or a "split introducer". While this arrangement permits insertion of the microdialysis probe and removal of the insertion cannula, the methods involved are relatively troublesome and require the use of two or more hands for maneuvering and splitting apart the insertion cannula, and for preventing the microdialysis probe from accompanying the pieces of the insertion cannula as they are removed. In addition, the possibility exists for pieces of the insertion cannula to be unintentionally left behind within the tissue. This is particularly dangerous where an incision has been made in order to insert the probe into an organ or other deep tissue, because the presence of debris within the body can cause harm to the subject, such as infection and/or internal bleeding.

Another problem associated with microdialysis of deeper tissues is the inability to accurately target specific tissue layers. Some microdialysis probes are at least partially constructed of materials that could theoretically be detected and imaged within biological tissue using the appropriate imaging equipment, such as x-ray, ultrasound, magnetic resonance imaging (MRI), and the like. For example, probes that are at least partially ultrasound-visible have been used to study transdermal penetration of a drug in superficial tissues. The appropriate position of the microdialysis probe is established by two-dimensional ultrasound and the distance between the skin surface and the tip of the microdialysis probe are measured (Muller, M. et al. [2000] "Microdialysis in Clinical Drug Delivery Studies" *Adv Drug Deliv Rev* 45(2–3):255–269). However, the mechanical designs of these probes do not permit highly accurate placement of the "active" portion of the probe, i.e., the dialysis membrane, within the target tissue.

Therefore, there is a need for a microdialysis probe design that permits the insertion of the probe into tissue, particularly deeper tissues, without the disadvantages associated with conventional microdialysis probe designs.

BRIEF SUMMARY OF THE INVENTION

The subject invention concerns methods and materials for accurately assessing the presence or absence of a substance within a medium, such as biological tissue.

The present invention relates to a microdialysis probe having a membrane portion; an outer tube for supplying perfusion fluid to the membrane portion, wherein the membrane portion is disposed at one end of the outer tube, hereafter referred to as the distal end; and an inner tube for transporting dialysate from the membrane portion, wherein the inner tube is arranged within the outer tube. Alternatively, the inner tube can supply perfusion fluid to the membrane portion and the outer tube can provide an exit for the dialysate from the membrane portion.

The microdialysis probe of the subject invention can include a guiding means, wherein the guiding means is at least partially composed of an imageable material and is located on or within the probe such that the guiding means is in a known spatial relationship with the membrane portion. Because the guiding means is at least partially composed of an imageable material and is in a known spatial relationship with the membrane portion, the position of the membrane portion within the surrounding medium can be readily determined using the appropriate sensing equipment. Therefore, it is possible to accurately guide the microdialysis probe, and more specifically, the membrane portion, to a particular location within the medium (e.g., a tissue layer, organ, tumor, cyst, or other structure). More specifically, the guiding means serves as a "visible" reference point for placement of the membrane portion within the medium. Therefore, the imageable material selected should have an image "signature" discernibly different from that of the medium into which the membrane portion is to be inserted.

The guiding means can be in a known position on or within the probe, such that imaging the guiding means provides information as to the location and, preferably, the spatial orientation of the membrane portion when inserted into a medium. Preferably, the guiding means provides information as to at least one geometric parameter of the membrane portion, such as a periphery or boundary of the membrane portion. More preferably, the guiding means delineates one or more boundaries of the membrane portion. For example, the guiding means can be approximately coextensive with one or more dimensions of the membrane portion, such as the length and/or the width of the membrane portion.

The subject invention further pertains to methods of sampling a substance within a medium, using the microdialysis probes of the subject invention. The microdialysis probes of the subject invention can be inserted into a given medium using an insertion means (e.g., insertion cannula). No portion of the probe has an outer diameter larger than the inner diameter of the insertion means utilized, thereby permitting a user to slide the insertion means over the microdialysis probe and completely withdraw the insertion means from the tissue. This feature is advantageous over conventional probes that have projecting components (e.g., handles, anchors, wings, hoses, and the like) that contribute to the outer diameter of the probes, making them larger in diameter than the inner diameter of the insertion means, which prevents complete removal of the insertion means. The subject invention further relates to methods of delivering a substance within a medium, using the microdialysis of the subject invention.

BRIEF DESCRIPTION OF THE DRAWINGS

FIG. 1A shows a side view of a microdialysis probe constructed in accordance with the present invention.

FIG. 1B shows a representative cross-sectional view of the microdialysis probe of FIG. 1A, with the cross-section of the probe taken along the line A—A of FIG. 1A.

FIG. 1C shows a representative cross-sectional view of the microdialysis probe of FIG. 1A, with the cross-section of the probe taken along the line B—B of FIG. 1A.

FIG. 1D shows a representative cross-sectional view of the microdialysis probe of FIG. 1A, with cross-section taken along the line C—C.

FIG. 1E shows a partially broken away view of the microdialysis probe of FIG. 1A.

FIG. 2A shows a side view of another microdialysis probe constructed in accordance with the present invention.

FIG. 2B shows a representative cross-sectional view of the microdialysis probe of FIG. 2A, with the cross-section of the probe taken along the line A—A of FIG. 2A.

FIG. 2C shows a representative cross-sectional view of the microdialysis probe of FIG. 2A, with the cross-section of the probe taken along the line B—B of FIG. 2A.

FIG. 2D shows a representative cross-sectional view of the microdialysis probe of FIG. 2A, with cross-section taken along the line C—C.

FIG. 2E shows a partially broken away view of the microdialysis probe of FIG. 2A.

FIG. 3A shows a side view of yet another microdialysis probe constructed in accordance with the present invention.

FIG. 3B shows a representative cross-sectional view of the microdialysis probe of FIG. 3A, with the cross-section of the probe taken along the line A—A of FIG. 3A.

FIG. 3C shows a representative cross-sectional view of the microdialysis probe of FIG. 3A, with the cross-section of the probe taken along the line B—B of FIG. 3A.

FIG. 3D shows a representative cross-sectional view of the microdialysis probe of FIG. 3A, with cross-section taken along the line C—C.

FIG. 3E shows a partially broken away view of the microdialysis probe of FIG. 3A.

DETAILED DISCLOSURE OF THE INVENTION

Figure 4A:
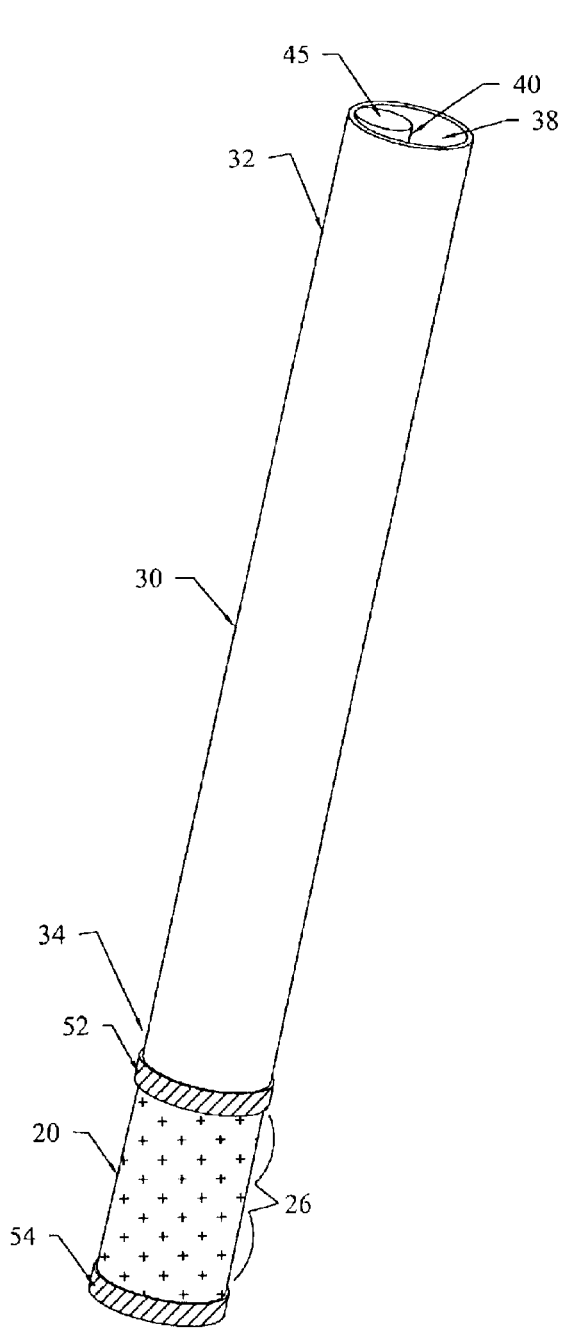
FIG. 4A shows a side view of another microdialysis probe constructed in accordance with the present invention.

The present invention relates to a microdialysis probe 10 including a membrane portion 20; an outer tube 30 for supplying perfusion fluid to the membrane portion 20, wherein the membrane portion 20 is disposed at one end of the outer tube 30, hereafter referred to as the distal end 32; and an inner tube 40 for transporting dialysate from the membrane portion 20, wherein the inner tube 40 is arranged within the outer tube 30.

The outer tube 30 is substantially hollow and has a proximal end 32, a distal end 34, an outer surface 36, an inner surface 38, and a lumen 35. The distal end 34 of the outer tube 30 has an opening 37 that is defined by an edge 39. The inner tube 40 is also substantially hollow and has a proximal end 42, a distal end 44, an outer surface 46, an inner surface 48, and a lumen 45. The distal end 44 of the inner tube 40 has an opening 47 adjacent, or in close proximity, to the membrane portion 20.

The microdialysis probe 10 of the subject invention can include a guiding means, wherein the guiding means is at least partially composed of an imageable material and is located on or within the probe 10 such that the guiding means is in a known spatial relationship with the membrane portion 20. As used herein, an "imageable material" includes those materials the location of which can be discerned within a given opaque, ambient medium (e.g., biological tissue), using the appropriate sensing equipment. Because the guiding means is in a known spatial relationship with the membrane portion 20, the position of the membrane portion 20 within the surrounding medium can be readily determined using the appropriate sensing equipment. Therefore, it is possible to accurately guide the microdialysis probe 10, and more specifically, the membrane portion 20, to a particular location (e.g., a tissue layer, organ, tumor, cyst, or other structure) within the medium. More specifically, the guiding means serves as a "visible" reference point for placement of the membrane portion 20 within the medium. Therefore, the imageable material selected should have an image "signature" discernibly different from that of the surrounding medium into which the membrane portion 20 is to be introduced.

In one embodiment, the imageable material is an echogenic material with an acoustic impedance different from that of the surrounding medium (i.e., high acoustic impedance differential), enabling the guiding means to be imaged using a sonic imaging device (e.g., ultrasound imaging equipment). A variety of materials that are echogenic (i.e., sound reflective) can be utilized, such as aluminum, hard plastic, sand, and metal particles. For example, the echogenic material can be any of those materials described in U.S. Pat. No. 5,201,314 and U.S. Pat. No. 6,106,473, or a combination of those materials. In another embodiment, the imageable material is a radio-opaque material that can be imaged with radiographic equipment (e.g., an x-ray machine or computed tomography (CT) scanner). In a further embodiment, the imageable material is a substance that can be imaged using magnetic resonance imaging/spectroscopy (MRI/MRS) equipment. Other imageable materials include those materials detectable through single photon emission tomography (SPECT) or positron emission tomography (PET), for example. The guiding means can be wholly or partly composed of the imageable material. For example, the imageable material can be in the form of a coating or film on an underlying substrate.

Contrast media, such as dyes, can also be used in conjunction with the appropriate imaging equipment in order to discern more details within the surrounding medium. For example, barium-containing and iodine-containing dyes can be administered in conjunction with x-ray or CT imaging. Gadolinium, for example, can be used in conjunction with MRI imaging.

The guiding means can be in a known position on or within the probe 10, such that imaging the guiding means provides information as to the location and, preferably, the spatial orientation of the membrane portion 20 when inserted into a medium. Preferably, the guiding means provides information as to at least one geometric parameter of the membrane portion 20, such as a periphery or boundary of the membrane portion 20. More preferably, the guiding means delineates one or more boundaries of the membrane portion 20.

The membrane portion 20 has an inner surface 27 and an outer surface 29. The membrane portion 20 can be any of a variety of shapes, such as a flat or curved sheet, or tubular. In one embodiment, the membrane portion 20 is shaped as a tube or cylinder, with a closed distal end 22 and a proximal end 24 having an opening 25, where the proximal end 24 is attached to the distal end 34 of the outer tube 30, effectively closing the distal end 34 of the outer tube 30.

In one embodiment, the guiding means is approximately coextensive with one or more dimensions of the membrane portion 20, such as the length 26 and/or the width 28 of the membrane portion 20. More preferably, the guiding means is approximately coextensive with the length 26 and the width 28 of the membrane portion 20.

The guiding means can be solid or hollow, and is not limited to any particular outer or cross-sectional shape. For example, the guiding means can have a cross-sectional shape that is circular, square, rectangular, triangular, or irregular. The guiding means can be a single structure or two or more structures.

In a specific embodiment, the guiding means is at least one projection 55 (e.g., shaft or wire) that extends longitudinally along at least part of the length 26 of the membrane portion 20. Preferably, the projection 55 is approximately co-extensive with the length 26 of the membrane portion 20, as shown in FIG. 1A (with the projection 55 shown in phantom within the membrane portion 20). FIGS. 1B–1D show representative cross-sectional views of the microdialysis probe of FIG. 1A, with the cross-section of the probe taken along the lines A—A, B—B, and C—C, respectively. FIG. 1E shows a side view of the same embodiment, with the outer tube 30 and membrane portion 20 partially broken away. The projection 55 effectively delineates the length 26 of the membrane portion 20, as shown in FIG. 1E, when the probe 50 is introduced into a medium and imaged using the appropriate sensing equipment. The projection 55 has a distal end 56 and a proximal end 58 and extends from a portion of the distal end 44 of the inner tube 40. The proximal end 58 of the projection 55 is attached to a portion of the distal end 44 of the inner tube 40. The proximal end 58 of the projection 55 can be attached to the distal end 44 of the inner tube 40 by any of a variety of means known in the art, such as with an adhesive.

In another embodiment, the inner tube 40 is composed of an imageable material, permitting the user to observe a more comprehensive image of the probe 10 within a medium. In this embodiment, the inner tube 40 can be composed of the same imageable material as the guiding means, or a different imageable material. In this embodiment, it is preferable that the inner tube 40 and the guiding means be of different diameter and/or shape to assist the user in discerning the position of the membrane portion 20 from the position of the inner tube 40 within the surrounding medium, which permits accurate insertion of the dialysis membrane 20 within a particular area of the medium.

In a specific embodiment, the inner tube 40 and the guiding means are composed of the same imageable material, have different diameters, and are integral, as shown in FIGS. 2A–2E. FIGS. 2B–2D show representative cross-sectional views of the microdialysis probe of FIG. 2A, with the cross-section of the probe taken along the lines A—A, B—B, and C—C, respectively. FIG. 2E shows a side view of the same embodiment, with the outer tube 30 and membrane portion 20 partially broken away. In this specific embodiment, the guiding means is a projection 55 that is integral with a portion of the distal end 44 of the inner tube 40. As can be seen in FIG. 2E, the inner tube 40 and the projection 55 have a different outer diameter. Specifically, the outer diameter of the projection 55 is about half the outer diameter of the inner tube 40. In addition, the outer tube 40 is approximately circular in cross-section while the projection 55 is approximately semi-circular in cross-section. The difference in the outer diameter of the inner tube 40 and the projection 55 assist the user in discerning the location of the membrane portion 20 from the location of the inner tube 40 within a medium, i.e., determining where the inner tube 40 ends and where the membrane portion 20 begins.

In another embodiment, the guiding means is attached to the outer tube distal end 34, instead of the inner tube distal end 44. The guiding means can be attached directly to the inner surface 38 of the outer tube 30 or attached to the membrane portion 20 where the membrane portion 20 attaches to the inner surface 38 of the outer tube 30. In a specific embodiment shown in FIGS. 3A–3E, the guiding means is a projection 55 and is attached to the outer tube distal end 34. FIGS. 3B–3D show representative cross-sectional views of the microdialysis probe of FIG. 3A, with the cross-section of the probe taken along the lines A—A, B—B, and C—C, respectively. FIG. 3E shows a side view of the same embodiment, with the outer tube 30 and membrane portion 20 partially broken away.

Alternatively, the guiding means can be located outside of the membrane portion 20, disposed on the outer tube 30 and in contact with the surrounding medium. For example, the guiding means can be attached to the edge 39 of the outer tube's distal end 34. The external guiding means can optionally surround the dialysis membrane 20, so long as a sufficient portion of the surface of the membrane portion 20 is exposed to the surrounding medium so that the membrane portion 20 can function (e.g., permit dialysis).

Figure 4B:
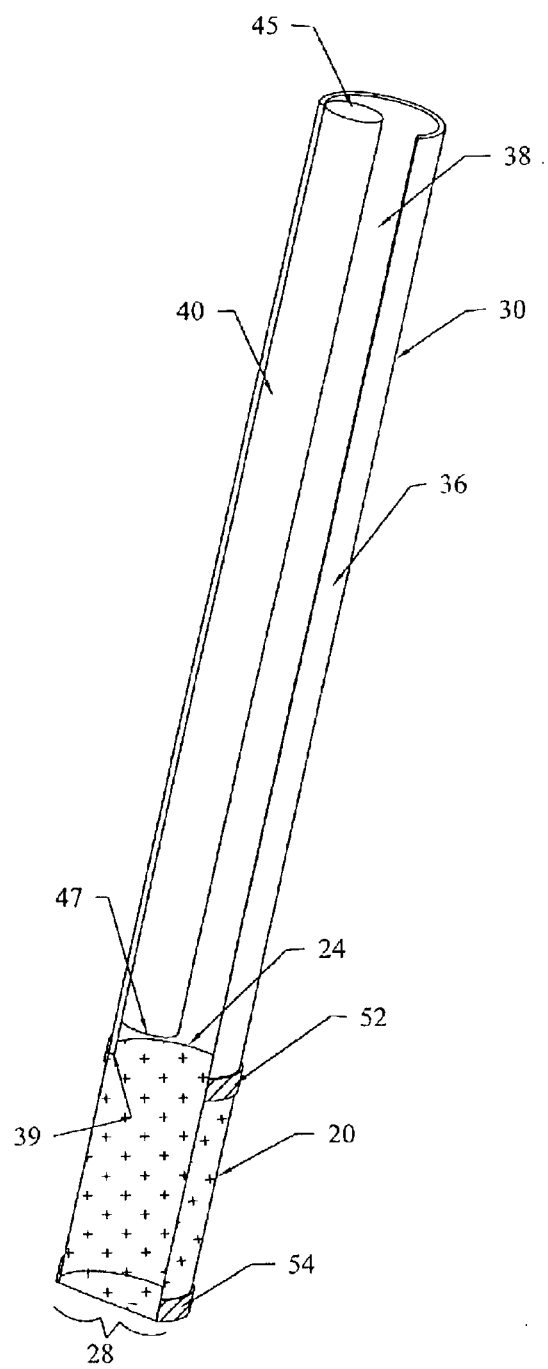
FIG. 4B shows a partially broken away view of the microdialysis probe of FIG. 4A.

In another specific embodiment, the guiding means includes one or more ring members that encircle the membrane portion 20 or the distal end 34 of the outer tube 30. Preferably, the guiding means includes two ring members, wherein a first ring member 52 is located adjacent, or in close proximity to, the proximal end 24 of the membrane portion 20 and a second ring member 54 is located adjacent, or in close proximity to, the distal end 22 of the membrane portion 20, and the two ring members 52 and 54 encircle the membrane portion 20, as shown in FIG. 4A. FIG. 4B shows a side view of the same embodiment, with the outer tube 30, membrane portion 20, and two ring members 52 and 54 partially broken away. When the probe 10 is introduced into a medium, the ring members 52 and 54 effectively delineate the boundaries of the membrane portion 20, e.g., the length 26 and the width 28.

The guiding means can be rigid or flexible. Preferably, the guiding means is flexible. The guiding means can be fixed to the probe 10 by a variety of means. For example, the guiding means can be bonded to the probe 50, as with adhesive, or made integral with a portion of the probe 10. If the guiding means is composed of a material that is elastic, the guiding means can be fixed to the probe 10 by virtue of its elasticity. For example, the ring members 52 and 54 can be composed of an elastic material and stretched around the probe 10.

In FIGS. 4A and 4B, the ring members 52 and 54 are located on the outer surface 36 of the outer tube's distal end 34 and the outer surface 29 of the membrane portion's distal end 22, respectively, but can be located anywhere on the probe 10, provided they delineate the boundaries of the membrane portion 20. For example, the first ring member 52 can be located on either the inner surface 38 of the outer tube's distal end 34 or on the inner surface 27 of the membrane portion's proximal end 24. Likewise, the second ring member 54 can be located on the inner surface 27 of the membrane portion's distal end 22.

If the guiding means is in contact with the inner surface 27 or the outer surface 29 of the membrane portion 20, the guiding means can also function to support the membrane (e.g., preventing its collapse). Alternatively, the guiding means can be in the form of imageable particulate matter that is located on or within the membrane portion 20. The guiding means can also be formulated as strands and woven or otherwise formulated into the membrane portion 20.

In another embodiment, the guiding means is disposed outside the membrane portion 20 and attached to, or integral with, the outer tube's distal end 34, preferably at it's distal edge 39. In addition, in this embodiment, the guiding means is shaped as a coil, encircling the membrane portion 20, and forming a point that is capable of piercing tissue. In this embodiment, the probe 10 can be inserted directly into tissue without the need for a needle to first pierce the tissue. The guiding means must leave enough of the membrane portion 20 exposed to the surrounding tissue in order to permit dialysis to take place.

The outer tube 30 can be rigid or flexible. Preferably, the outer tube 30 is flexible. More preferably, the outer tube 30 is compressible in that it can be compressed (as between a thumb and forefinger) against the inner tube 40 contained therein. If the microdialysis probe 10 is to be inserted into biological tissue, the outer tube 30 is preferably composed of a material that is biocompatible. In one embodiment, the outer tube 30 is plastic. Examples of suitable plastics include, but are not limited to, urethane, ethylene, silicone, polyethylene, polyurethane, polyvinyl chloride, polypropylene, polyester, and polytetrafluoroethylene.

Preferably, the outer tube 30 is substantially circular in cross-section, such that it is easily inserted into tissue with insertion means (e.g., insertion cannula) having lumens of standard shape. However, the outer tube 30 can have any of a variety of cross-sectional shapes, such as, but not limited to, oval, triangular, and square.

The OD (outside diameter) of the outer tube 30 can be sufficiently small to allow the probe 10 to be inserted using insertion means (e.g., insertion cannulas) having various sized lumens. In addition, no portion of the probe, including the outer tube 30, should have an OD larger than the ID (inner diameter) of the insertion means utilized, thereby permitting the insertion means to slide over the microdialysis probe and be completely withdrawn from the tissue. For example, if the insertion means has an ID of 0.5 millimeters, the OD of the probe 10 should be smaller than 0.5 millimeters and be sufficiently small to slidably pass through the lumen of the insertion means. This feature is advantageous over probes that have protruding components (e.g., handles, anchors, and the like) the make the OD of the probe larger than the ID of the insertion means, which prevents complete removal of the insertion means.

The outer tube 30 of the microdialyis probe 10 can be composed of a compressible material, such that the outer tube 30 can be readily compressed (as with a thumb and forefinger). Preferably, the outer tube 30 is capable of being compressed to an extent that the inner surface 38 of the outer tube 30 can make contact with the outer surface 46 of the inner tube 40 at the area of compression. This feature increases the versatility of the microdialysis probe 10, permitting the probe to be used with a variety of insertion means having various inner diameters. This feature also facilitates the complete removal of the insertion means utilized, by merely sliding the insertion means off the microdialysis probe 10. Depending upon the relative sizes of the OD of the outer tube 30 and ID of the insertion means utilized, the outer tube 30 can be compressed, if required, to fit within the insertion means.

The ID of the outer tube 30 can be in the range of about 300 micrometers to about 1000 micrometers. Preferably, the ID of the outer tube 30 is in the range of about 400 micrometers to about 700 micrometers. More preferably, the ID of the outer tube 30 is about 500 micrometers. The outer tube 30 can be any length suited to the particular application. For example, if the probe is being inserted into muscle, the length of the outer tube 30 can be in the range of about 5 centimeters to about 30 centimeters, and is preferably about 10 centimeters. If the probe is being inserted into lung, the length of the outer tube 30 can be in the range of about 20 centimeters to about 80 centimeters, and is preferably about 50 centimeters. Preferably, the outer tube 30 is about 70 centimeters in length.

The inner tube 40 can be rigid or flexible. Preferably, the inner tube 40 is flexible. In one embodiment, the inner tube 40 is plastic. Examples of suitable plastics include, but are not limited to, urethane, ethylene, silicone, polyethylene, polyurethane, polyvinyl chloride, polypropylene, polyester, and polytetrafluoroethylene.

The ID of the inner tube 40 can be in the range of about 25 micrometers to about 700 micrometers. Preferably, the ID of the inner tube 40 is in the range of about 100 micrometers to about 500 micrometers. More preferably, the ID of the inner tube 40 is about 300 micrometers. The length of the inner tube 40 can be about the same as the length of the outer tube 30. The inner tube 40 can be longer or shorter than the outer tube 30, depending, for example, upon whether or not the inner tube distal end 44 terminates at a point before or after (beyond) the outer tube distal end 34 terminates.

The inner tube 40 can be attached directly or indirectly to the outer tube 30 and is preferably attached directly to the inner surface 38 of the outer tube 30. The inner tube 40 can be attached to the outer tube 30 continuously, or at discrete points. Preferably, the outer tube 30 has a longitudinal axis that extends parallel to the longitudinal axis of the inner tube 40. In one embodiment, the outer tube 30 and the inner tube 40 are concentrically arranged. In this embodiment, the inner tube 40 runs through the center of the outer tube 30, both the inner and outer tubes having about the same longitudinal axis.

Figure 5A:
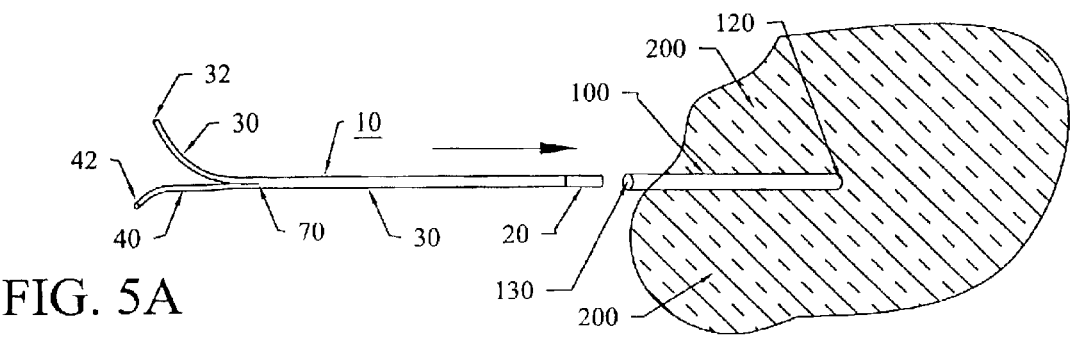
FIGS. 5A–5D show a schematic illustration of a method for inserting a microdialysis probe of the subject invention into biological tissue using an insertion cannula.
Figure 5B:
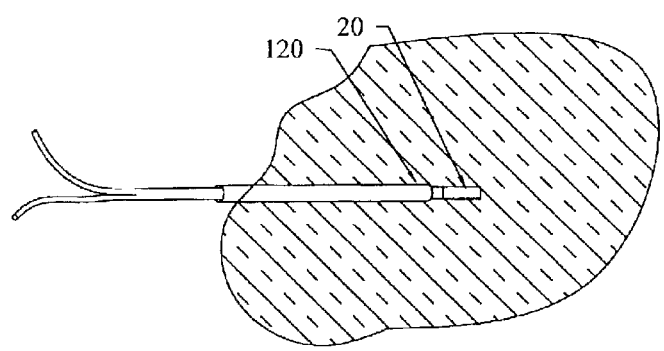
Figure 5C:
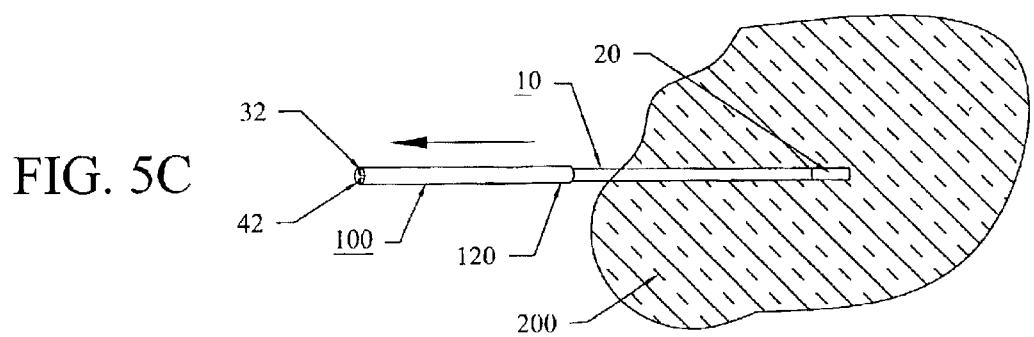
Figure 5D:
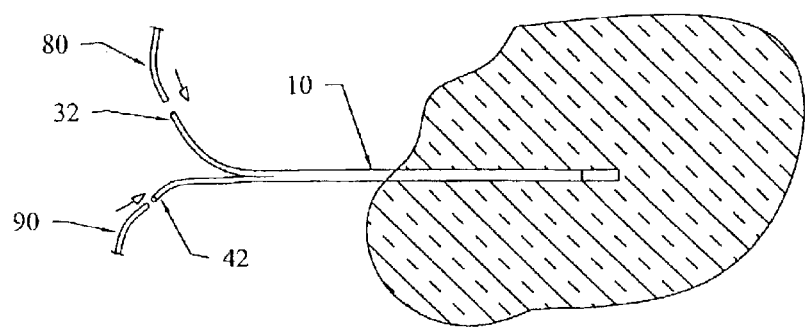

At a desired point along the length of the outer tube 30, an opening 70 can be arranged in the outer tube 30 to allow the proximal end 42 of the inner tube 40 to pass there through in a fluid-tight manner. At this junction, the inner tube 40 is no longer contained within the outer tube 30. The inner tube 40 and the outer tube 30 can be attached at or along their outer surfaces 46 and 36, respectively, or be completely bifurcated proximal to the opening 70, as shown in FIG. 5a.

The proximal ends of the outer tube 32 and inner tube 42 can be connected, respectively, to a source of perfusion fluid and collection means (e.g., vial holder) appropriate for the particular use of the probe (e.g., taking samples, perfusing drugs, and the like) either directly or indirectly, via inlet tubing 80 and outlet tubing 90. The inlet tubing 80 and outlet tubing 90 can be composed of a variety of materials, such as fluoroplastic materials (e.g., FEP, PFA, MFA, PTFE, PVDF). Preferably, the inlet tubing 80 and outlet tubing 90 are composed of FEP (fluorinated ethylene propylene). The inlet and outlet tubing 80 and 90 can be corrugated for ease of flexure and optimal bend radius. The inlet and outlet tubing 80 and 90 can be attached to (e.g., placed in fluid communication with) the proximal ends 32 and 42 of the outer and inner tubes 30 and 40, respectively (or vice-versa), by connecting means known to those skilled in the art. Connecting means include polyurethane connectors or adaptors, for example.

The inlet tubing 80 is preferably attached to, or otherwise in operable communication with, a liquid pump. The pump can be a mechanically driven syringe pump, for example. The outlet tubing 90 serves as the means to collect the dialysate from the inner tube 40 of the probe once the substance of interest (e.g., an analyte) has diffused across the membrane portion 20, and thus serves as an egress for the dialysate from the probe.

While the outer tube 30 has been described as supplying perfusion fluid to the membrane portion 20 and the inner tube 40 has been described as transporting the dialysate from the membrane portion 20, it should be understood that the functions of the outer tube 30 and inner tube 40 can be reversed. Specifically, the inner tube 40 can supply perfusion fluid to the membrane portion 20 and the outer tube 30 can transport the collected dialysate out of the probe 10.

The membrane portion 20 serves the primary function of creating a fluid compartment within the surrounding medium, such as biological tissue, and allows diffusion of solutes across its surface into the probe 10. The membrane portion 20 can be a dialysis membrane that functions on the basis of molecular weight and/or other suitable criterion (e.g., enzyme affinity, sulfide group affinity). A membrane with relatively low molecular weight cut off purifies the sample by excluding large molecules, while a relatively high molecular weight cut off recovers large substances, such as peptides or proteins. A longer membrane provides a better recovery of the substance(s) of interest, but the length of the membrane is also limited by the size of the tissue structure (e.g., organ) or region of interest.

The membrane portion 20 is semi-permeable. The membrane portion 20 can be rigid or flexible. Preferably, the membrane portion 20 is flexible. If the microdialysis probe is intended for use in biological tissue, the membrane portion 20 is preferably composed of a biocompatible material, such as PES (polyethersulfone), PVDF (polyvinylidene fluoride), PTFE (polytetrafluoroethylene), polycarbonate, or cuprophane.

The membrane portion 20 is secured about its entire periphery to the adjacent portion of the outer tube 30. Preferably, the membrane portion 20 is disposed at the distal end 34 of the outer tube 30. More preferably, the membrane portion 20 is attached either to the inner surface 38 of the outer tube distal end 34, or to the edge 39 of the outer tube distal end 34. The latter arrangement ensures that when the probe 10 is removed from the medium, the chance of the membrane portion 20 being separated from, or stripped off, the outer tube 30 is minimized. This arrangement also minimizes the OD of the probe at the joint between the outer tube distal end 34 and the membrane portion 20. The membrane portion 20 can be attached to the outer tube 30 by a variety of means, such as, but not limited to, an adhesive, a mating flange, or be screwed on by threads.

Alternatively, the outer tube 30 can define an aperture or window that is occupied by, or otherwise exposing, the membrane portion 20, as described in U.S. Pat. No. 4,694,832; in which case, the outer tube 30 can be closed at its distal end 34 in order to facilitate dialysis through the membrane portion 20. The aperture (and the membrane portion 20) can extend partially or fully around the outer tube 30. The size and shape of the aperture can be varied, depending upon the desired size and shape of the exposed surface of the membrane portion 20.

The membrane portion 20 can be of a shape such that the membrane portion 20 has an ID and OD. For example, the membrane portion 20 can be tubular or cylindrical in shape. The membrane portion 20 OD can be in the range of about 300 micrometers to about 1000 micrometers. Preferably, the OD of the membrane portion 20 is in the range of about 400 micrometers to about 700 micrometers. More preferably, the OD of the membrane portion 20 is about 500 micrometers. The ID of the membrane portion 20 will then depend upon the thickness of the membrane portion 20.

The thickness of the membrane portion 20 can vary with the material utilized and the flow-rate desired. For example, the membrane portion 20 can have a thickness in the range of about 25 micrometers to about 250 micrometers.

The membrane portion 20 can be in the range of about 1 millimeter to about 100 millimeters in length. Preferably, the length of the membrane portion 20 is in the range of about 10 millimeters to about 50 millimeters. Preferably, the membrane portion 20 is about 20 millimeters in length.

The difference in concentration over the membrane portion 20 dictates in which direction the gradient is established. Therefore, it is possible to collect an endogenous compound at the same time an exogenous compound, e.g., a drug, is being introduced into a tissue.

If the surrounding medium is biological tissue, for example, the gradient of a particular compound depends upon the difference in concentration between the perfusion fluid (i.e., perfusate) and the extracellular fluid, as well as upon the velocity of flow inside the microdialysis probe 10. The absolute recovery (e.g., mol/time unit) of a substance from the tissue depends on (1) the "cut off" of the dialysis membrane, which is usually defined as the molecular weight (e.g., in Daltons) at which 80% of the molecules are prevented from passing through the membrane portion, and is at least partly a function of pore size; (2) the length of the membrane portion 20; (3) the flow of the perfusion fluid; and (4) the diffusion coefficient of the compound through the extracellular fluid. The reverse holds true for substances entering the tissue from the probe 10. The above parameters can be optimized by one of ordinary skill in the art, based upon the particular application.

The perfusion fluid contains ingredients selected either for minimal perturbation of the chemical environment within the surrounding medium, or contains substances added for diagnostic, analytical, or therapeutic applications, into the dialysis probe. For biological applications, the perfusion fluid is preferably similar in composition to the extracellular fluid. However, the composition of the perfusion fluid can be varied in order to influence the membrane portion's function in the region of interest. For example, the ionic composition of the perfusion fluid can be changed, e.g., changing the concentration of sodium, potassium, or calcium.

Through reverse microdialysis, the probes of the subject invention can be utilized as delivery tools. Various substances can also be administered to the ambient medium via addition to the dialysis perfusion fluid. Substances that can be administered to the ambient medium include, but are not limited to, endogenous mediators, such as cytokines or hormones; and exogenous drugs, such as glucocorticoids, non-steroidal anti-inflammatory drugs (NSAIDS), opioids, allergens, acetyl-salicylic acid, or analgesics.

Because the introduction of a probe into the tissue will almost always cause some trauma to the tissue, sampling is preferably delayed for a time following insertion of the probe, in order to reach steady state or baseline conditions.

The dialysate can be collected using a variety of sample collecting equipment. Preferably, a sample collector is utilized that collects the dialysate in microvials designed for low evaporation and minute volumes. The samples can be analyzed, for example, at the bedside or lab bench. Alternatively, the samples can be stored for later use.

While the microdialysis probe of the subject invention is particularly useful for continuous monitoring of substances in biological tissue in vivo, such as human and animal tissue, the probe of the subject invention can also be used in various media in vitro, such as cell cultures, fermentation vessels, and the like.

Methods of sampling and/or drug delivery using the microdialysis probes of the subject invention are described in Examples 1 and 2, and illustrated in FIGS. 5A–5D. As previously indicated, the microdialysis probes of the subject invention are advantageous over conventional probes that have projecting components (e.g., handles, anchors, wings, hoses, and the like) that contribute to the OD of the probes, making them larger in OD than the ID of the insertion means, which prevents complete removal of the insertion means.

Figure 6A:
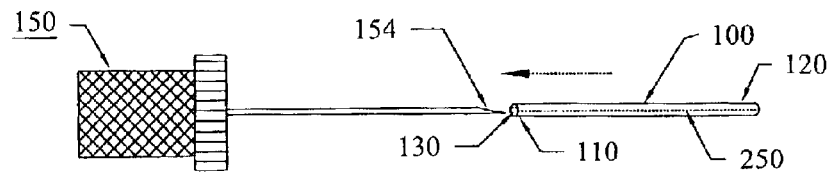
FIGS. 6A–6E show a schematic illustration of a method for inserting a conventional microdialysis probe into biological tissue using a rupturable insertion cannula.
Figure 6B:
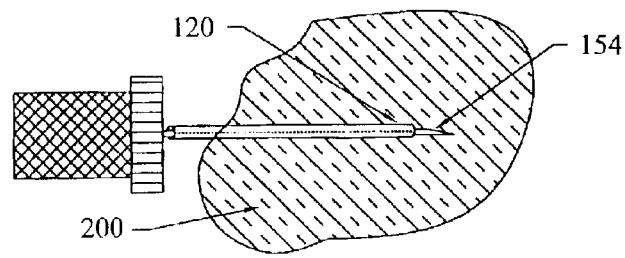
Figure 6C:
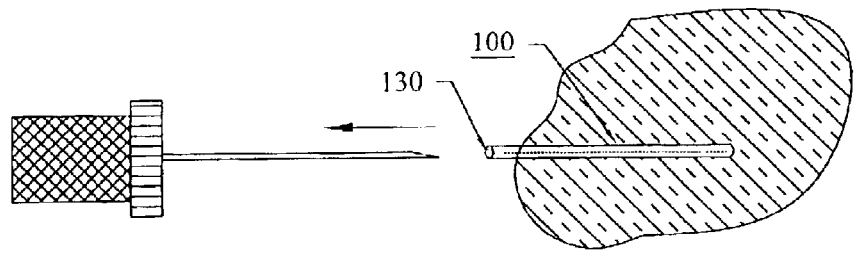
Figure 6D:
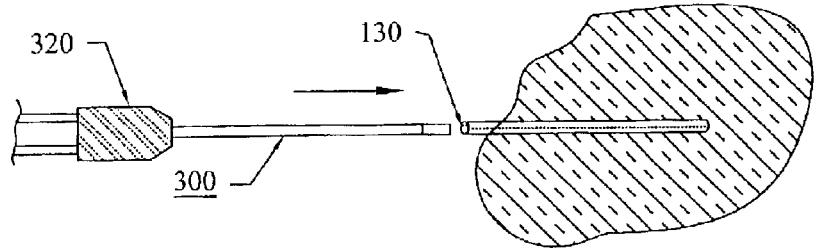
Figure 6E:
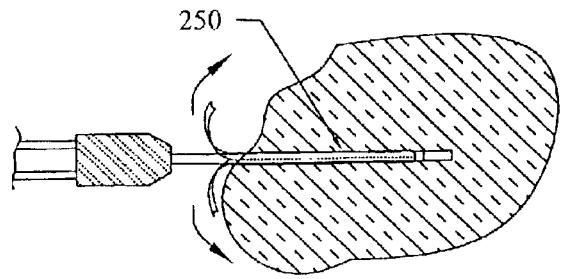

A method for inserting a conventional microdialysis probe 300 into tissue 200 using a rupturable insertion cannula 100 is illustrated in FIGS. 6A–6E. As shown in FIGS. 6A–6B, a needle 150 is inserted into the proximal end 110 of the rupturable insertion cannula 100, through the lumen 130, such that the tip 154 of the needle 150 extends out of the distal end 120 of the rupturable insertion cannula 100. The needle 150 and the rupturable insertion cannula 100 are then inserted into tissue 200. As shown in FIG. 6C, the needle 150 is then removed from the rupturable insertion cannula 100 and replaced with the conventional microdialysis probe 300. As shown in FIG. 6D, the conventional microdialysis probe 300 typically has a connecting part 320, or some other protruding component, that makes the conventional microdialysis probe 300 larger in OD than the ID (e.g., of the lumen 130) of the rupturable insertion cannula 100. Therefore, it is necessary to construct the rupturable insertion cannula 100 with longitudinal weakenings 250 (e.g., perforations). As shown in FIGS. 6D–6E, after the conventional microdialysis probe 300 is inserted into the rupturable insertion cannula 100, the rupturable insertion cannula 100 can be pulled apart into two or more pieces and eliminated, leaving only the conventional microdialysis probe 300 positioned within the tissue 200.

All patens, patent applications, provisional applications, and publications referred to or cited herein are incorporated herein by reference in their entirety to the extent they are not inconsistent with the explicit teachings of this specification.

Following are examples which illustrate procedures, including the best mode, for practicing the subject invention. These examples should not be construed as limiting. All percentages are by weight and all solvent mixture proportions are by volume unless otherwise noted.

EXAMPLE 1

Insertion of the Microdialysis Probe Through the Skin

Insertion of the microdialyis probe of the subject invention into a medium will now be described, using human tissue as the exemplified medium. The microdialysis probe of the subject invention can be inserted into biological tissue 200 with insertion means, such as an insertion cannula 100. The insertion cannula 100 has a proximal end 110, a distal end 120, and a lumen 130. A puncture means, such as a needle 150, can be used to puncture the tissue 200. The needle 150 has a proximal end 152 and a pointed distal end 154, and is inserted into the lumen 130 of the insertion cannula 100 so that the pointed distal end 154 of the needle 150 extends out of the distal end 120 of the insertion cannula 100. The needle 150 and insertion cannula 100 are then inserted into the tissue 200, with the pointed end 154 of the needle 150 piercing the skin. The needle 150 is then withdrawn from the lumen 130 of the insertion cannula 100, leaving the insertion cannula 100 within the tissue 200. The microdialysis probe 10 is then inserted into the lumen 130 of the insertion cannula 100. Because the outer tube 30 of the probe 10 can be composed of a compressible material, the probe 10 can be inserted into insertion means of a variety of sizes (i.e., inner diameters).

When inserted into the insertion cannula 100, the membrane portion 20 preferably extends a small distance beyond the distal end 120 of the insertion cannula 100, into the tissue 200, occupying the space that the pointed end 154 of the needle 150 previously occupied. The insertion cannula 100 is then withdrawn from the tissue 200, slid over the microdialysis probe 10, and set aside or discarded, leaving the microdialysis probe 10 within the tissue 200. The proximal ends 42 and 32 of the inner and outer tubes 40 and 30 can then be attached to inlet and outlet tubing 80 and 90 for sampling and/or drug delivery.

EXAMPLE 2

Insertion of the Microdialysis Probe into the Lung

The microdialysis probe of the subject invention can be inserted into an internal organ, such as a lung, by first making a surgical incision in the skin. The chest wall is then surgically opened to expose the chest cavity. Puncture means, such as a needle 150, is inserted into the lumen 130 of the insertion cannula 100 so that the pointed distal end 154 of the needle 150 extends out of the distal end 120 of the insertion cannula 100. The needle 150 and insertion cannula 100 are then inserted into the tissue 200, with the pointed end 154 of the needle 150 piercing the outer tissue of the lung. The needle 150 is then withdrawn from the lumen 130 of the insertion cannula 100, leaving the insertion cannula 100 within the outer tissue of the lung. The microdialysis probe 10 is then inserted into the lumen 130 of the insertion cannula 100. The membrane portion 20 preferably extends a small distance beyond the distal end 120 of the insertion cannula 100, into the tissue, occupying the space that the pointed end 154 of the needle 150 previously occupied. The insertion cannula 100 is then withdrawn from the tissue 200, slid over the microdialysis probe 10, and set aside or discarded, leaving the microdialysis probe 10 within the tissue 200. The proximal ends 42 and 32 of the inner and outer tubes 40 and 30 can then be attached to inlet and outlet tubing 80 and 90 for sampling and/or drug delivery.

Optionally, the incision made in the chest can be substantially closed, leaving either the proximal ends 42 and 32 of the inner and outer tubes 40 and 30, or the inlet and outlet tubing 80 and 90, extending from the subject's chest.

It should be understood that the examples and embodiments described herein are for illustrative purposes only and that various modifications or changes in light thereof will be suggested to persons skilled in the art and are to be included within the spirit and purview of this application and the scope of the appended claims.

What is claimed is:

1. A microdialysis probe comprising:
    a semi-premeable membrane portion;
    an outer tube, wherein said outer tube has a proximal end, a distal end, an inner surface, and an outer surface, wherein said membrane portion is disposed on said distal end of said outer tube;

an inner tube, wherein said inner tube has a proximal end, a distal end, an inner surface, and an outer surface, and wherein said inner tube is arranged within said outer tube;

and a guiding means located on said probe in a known spatial relationship with said membrane portion such that imaging said guiding means provides information as to the location of said membrane portion when said probe is inserted into a medium.

2. The microdialysis probe of claim 1, wherein said guiding means comprises an imageable material.

3. The microdialysis probe of claim 1, wherein said guiding means comprises an imageable material having an image signature that is discernable from that of biological tissue.

4. The microdialysis probe of claim 1, wherein said guiding means comprises an echogenic material.

5. The microdialysis probe of claim 1, wherein said guiding means comprises an echogenic material having an acoustic impedance different from that of the surrounding medium into which said guiding means is introduced.

6. The microdialysis probe of claim 1, wherein said guiding means comprises an imageable material selected from the group consisting of aluminum, plastic, sand, and metal particles.

7. The microdialysis probe of claim 1, wherein said guiding means comprises an imageable material that is radio-opaque.

8. The microdialysis probe of claim 1, wherein said guiding means comprises an imageable material that can be imaged with magnetic resonance imaging or magnetic resonance spectroscopy.

9. The microdialysis probe of claim 1, wherein said guiding means comprises an imageable material that can be imaged with single photon emission tomography or positron emission tomography.

10. The microdialysis probe of claim 1, wherein said guiding means comprises an imageable material that is formulated as a coating on said microdialysis probe.

11. The microdialysis probe of claim 1, wherein said guiding means also provides information as to the spatial orientation of said membrane portion when said membrane portion is inserted into a medium and when said guiding means is imaged.

12. The microdialysis probe of claim 1, wherein said guiding means provides information as to at least one geometric parameter of said membrane portion when said guiding means is imaged.

13. The microdialysis probe of claim 1, wherein said membrane portion is defined by boundaries, and wherein said guiding means occupies an area on said microdialysis probe such that said guiding means delineates one or more of said boundaries when said guiding means is imaged.

14. The microdialysis probe of claim 13, wherein said guiding means is coextensive with one or more of said boundaries.

15. The microdialysis probe of claim 1, wherein said membrane portion has a length and a width, and wherein said guiding means is coextensive with said length of said membrane portion, or said width of said membrane portion, or both said length and said width of said membrane portion.

16. The microdialysis probe of claim 1, wherein said guiding means has a cross-sectional shape selected from the group consisting of circular, square, rectangular, triangular, and irregular.

17. The microdialysis probe of claim 1, wherein said guiding means comprises two or more structures on said probe.

18. The microdialysis probe of claim 1, wherein said inner tube is composed of an imageable material.

19. The microdialysis probe of claim 1, wherein said membrane portion has a length, and wherein said guiding means comprises at least one projection that extends longitudinally along at least part of the length of said membrane portion.

20. The microdialysis probe of claim 19, wherein said projection is a shaft or wire.

21. The microdialysis probe of claim 19, wherein said projection has a proximal end and a distal end, and wherein said proximal end of said projection is attached to said distal end of said inner tube.

22. The microdialysis probe of claim 19, wherein said inner tube is composed of an imageable material and said projection is integral with said distal end of said inner tube.

23. The microdialysis probe of claim 1, wherein said inner tube and said guiding means are composed of an imageable material.

24. The microdialysis probe of claim 23, wherein said inner tube and said guiding means are composed of the same imageable material.

25. The microdialysis probe of claim 1, wherein said outer tube is substantially circular in cross-section.

26. The microdialysis probe of claim 1, wherein said guiding means is attached to said distal end of said outer tube.

27. The microdialysis probe of claim 1, wherein said guiding means is attached to said inner surface of said outer tube.

28. The microdialysis probe of claim 1, wherein said membrane portion is attached to said inner surface of said outer tube, and wherein said guiding means is attached to said membrane portion adjacent to where said membrane portion is attached to said inner surface of said outer tube.

29. The microdialysis probe of claim 1, wherein said guiding means is attached to said distal end of said outer tube, and wherein said guiding means surrounds said membrane portion.

30. The microdialysis probe of claim 1, wherein said guiding means comprises one or more ring members that encircle said membrane portion.

31. The microdialysis probe of claim 1, wherein said guiding means comprises one or more ring members that encircle said distal end of said outer tube.

32. The microdialysis probe of claim 1, wherein said outer tube has a longitudinal axis, wherein said inner tube has a longitudinal axis, and wherein said longitudinal axis of said outer tube is parallel to said longitudinal axis of said inner tube.

33. The microdialysis probe of claim 1, wherein said guiding means is flexible.

34. The microdialysis probe of claim 1, wherein said guiding means is rigid.

35. The microdialysis probe of claim 1, wherein said guiding means is shaped as a coil, and wherein said guiding means encircles said membrane portion.

36. The microdialysis probe of claim 1, wherein said inner tube and said outer tube are concentric.

37. The microdialysis probe of claim 1, wherein said inner tube and said outer tube are not concentric.

38. The microdialysis probe of claim 1, wherein said inner tube is longer than said outer tube.

39. The microdialysis probe of claim 1, wherein said inner tube is shorter than said outer tube.

40. The microdialysis probe of claim 1, wherein said outer tube is flexible.

41. The microdialysis probe of claim 1, wherein said outer tube is compressible.

42. The microdialysis probe of claim 1, wherein said outer tube is plastic.

43. The microdialysis probe of claim 1, wherein said outer tube is composed of a material selected from the group consisting of urethane, ethylene, silicone, polyethylene, polyurethane, polyvinyl chloride, polypropylene, polyester, and polytetrafluorothylene.

44. The microdialysis probe of claim 1, wherein said outer tube has a cross-sectional shape selected from the group consisting of circle, oval, triangle, and square.

45. The microdialysis probe of claim 1, wherein said outer tube has an inner diameter within the range of about 300 micrometers to about 1000 micrometers.

46. The microdialysis probe of claim 1, wherein said inner tube has an inner diameter within the range of about 25 micrometers and 700 micrometers.

47. A microdialysis probe comprising:
a semi-permeable membrane portion;
an outer tube, wherein said outer tube has a proximal end, a distal end, an inner surface, and an outer surface, wherein said distal end of said outer tube is closed, and wherein said outer surface of said outer tube defines an aperture exposing said membrane portion;
an inner tube, wherein said inner tube has a proximal end, a distal end, an inner surface, and an outer surface, and wherein said inner tube is arranged within said outer tube;
and a guiding means located on said probe in a known spatial relationship with said membrane portion such that imaging said guiding means provides information as to the location of said membrane portion when said probe is inserted into a medium.

48. A microdialysis probe comprising:
a semi-premeable membrane portion;
an outer tube, wherein said outer tube has a proximal end and a distal end, and wherein said membrane portion is disposed on said distal end of said outer tube; and
an inner tube, wherein said inner tube is arranged within said outer tube, and wherein said inner tube comprises an imageable material.

49. The microdialysis probe of claim 48, wherein said imageable material has an image signature that is discernable from that of surrounding medium into which said membrane portion is introduced.

50. The microdialysis probe of claim 48, wherein said imageable material is an echogenic material.

51. The microdialysis probe of claim 48, wherein said imageable material is selected from the group consisting of aluminum, plastic, sand, and metal particles.

52. The microdialysis probe of claim 48, wherein said imageable material is radio-opaque.

53. The microdialysis probe of claim 48, wherein said imageable material can be imaged with magnetic resonance imaging or magnetic resonance microscopy.

54. The microdialysis probe of claim 48, wherein said imageable material can be imaged with single photon emission tomography or positron emission tomography.

55. A microdialysis probe comprising:
a membrane portion;
an outer tube, wherein said outer tube has a proximal end, a distal end, an inner surface, and an outer surface, wherein said membrane portion is disposed on said distal end of said outer tube;
an inner tube, wherein said inner tube has a proximal end, a distal end, an inner surface, and an outer surface, wherein said inner tube is arranged within said outer tube, and wherein said inner tube is semi-circular in cross-section;
and a guiding means located on said probe in a known spatial relationship with said membrane portion.

56. A microdialysis probe comprising:
a membrane portion;
an outer tube, wherein said outer tube has a proximal end, a distal end, an inner surface, and an outer surface, wherein said membrane portion is disposed on said distal end of said outer tube;
an inner tube, wherein said inner tube has a proximal end, a distal end, an inner surface, and an outer surface, and wherein said inner tube is arranged within said outer tube;
and a guiding means located on said probe in a known spatial relationship with said membrane portion, wherein said membrane portion has a closed distal end and a proximal end having an opening, wherein said proximal end of said membrane portion is attached to said distal end of said outer tube, wherein said guiding means comprises a first ring member and a second ring member, and wherein said first ring member is located on or adjacent to said proximal end of said membrane portion and wherein said second ring member is located on or adjacent to said distal end of said membrane portion.

57. The microdialysis probe of claim 56, wherein said first ring member is located on said inner surface of said distal end of said outer tube.

58. The microdialysis probe of claim 56, wherein said membrane portion has an outer surface and an inner surface, and wherein said first ring member is located on said inner surface of said proximal end of said membrane portion.

59. The microdialysis probe of claim 58, wherein said second ring member is located on said inner surface of said distal end of said membrane portion.

60. A method for introducing a microdialysis probe into a medium, comprising:
inserting the microdialysis probe of claim 1 into the medium.

61. The method of claim 60, wherein the medium is biological tissue.

62. The method of claim 61, wherein said method further comprises puncturing the biological tissue prior said inserting.

63. The method of claim 60, wherein the medium is an internal organ.

64. The method of claim 60, wherein the guiding means comprises an imageable material, and wherein said met no further comprises imaging the guiding means within the medium.

65. A method for introducing a microdialysis probe into a medium, comprising:
inserting the microdialysis probe of claim 47 into the medium.

66. The method of claim 65, wherein the medium is biological tissue.

67. The method of claim 66, wherein said method further comprises puncturing the biological tissue prior said inserting.

68. The method of claim 65, wherein the medium is an internal organ.

69. The method of claim 65, wherein the guiding means comprises an imageable material, and wherein said method further comprises imaging the guiding means within the medium.

70. A method for introducing a microdialysis probe into a medium, comprising:

inserting the microdialysis probe of claim 48 into the medium.

71. The method of claim 70, wherein the medium is biological tissue.

72. The method of claim 71, wherein said method further comprises puncturing the biological tissue prior said inserting.

73. The method of claim 70, wherein the medium is an internal organ.

74. A method for introducing a microdialysis probe into a medium, comprising:

inserting the microdialysis probe of claim 55 into the medium.

75. The method of claim 74, wherein the medium is biological tissue.

76. The method of claim 75, wherein said method further comprises puncturing the biological tissue prior said inserting.

77. The method of claim 74, wherein the medium is an internal organ.

78. A method for introducing a microdialysis probe into a medium, comprising:

inserting the microdialysis probe of claim 56 into the medium.

79. The method of claim 78, wherein the medium is biological tissue.

80. The method of claim 79, wherein said method further comprises puncturing the biological tissue prior said inserting.

81. The method of claim 78, wherein the medium is an internal organ.

\* \* \* \* \*

UNITED STATES PATENT AND TRADEMARK OFFICE
CERTIFICATE OF CORRECTION

PATENT NO. : 6,904,309 B2  Page 1 of 1
DATED : June 7, 2005
INVENTOR(S) : Hartmut Derendorf and Markus Mueller It is certified that error appears in the above-identified patent and that said Letters Patent is hereby corrected as shown below:

<u>Title page,</u>
Item [57], ABSTRACT,
Line 5, "can the be" should read -- can then be --.

<u>Column 14,</u>
Line 63, "semi-premeable" should read -- semi-permeable --.

<u>Column 17,</u>
Line 35, "semi-premeable" should read -- semi-permeable --.

<u>Column 18,</u>
Line 50, "said met no" should read -- said method --.

Signed and Sealed this

Fourth Day of April, 2006

JON W. DUDAS
*Director of the United States Patent and Trademark Office*